(12) United States Patent
Vogel et al.

(10) Patent No.: US 8,342,841 B2
(45) Date of Patent: Jan. 1, 2013

(54) PROCEDURE SPECIFIC STORAGE BLOCK FOR HOLDING IMPLANT CONTAINERS AND SURGICAL TOOLS

(75) Inventors: Tyson Vogel, San Diego, CA (US); Charles Howlett, Laguna Beach, CA (US); Mojtaba Esfahni, Del Mar, CA (US)

(73) Assignee: Zimmer Dental, Inc., Carlsbad, CA (US)

( * ) Notice: Subject to any disclaimer, the term of this patent is extended or adjusted under 35 U.S.C. 154(b) by 108 days.

(21) Appl. No.: 12/512,462

(22) Filed: Jul. 30, 2009

(65) Prior Publication Data

US 2010/0028828 A1    Feb. 4, 2010

Related U.S. Application Data

(60) Provisional application No. 61/084,815, filed on Jul. 30, 2008.

(51) Int. Cl.
*A61C 13/38* (2006.01)

(52) U.S. Cl. ......... 433/77; 206/63.5; 206/362; 206/363; 206/379; 206/368; 312/902; 312/209

(58) Field of Classification Search ............ 433/77, 433/126, 79; 312/209, 902; 206/369, 63.5, 206/368, 363, 379
See application file for complete search history.

(56) References Cited

U.S. PATENT DOCUMENTS

| | | | | |
|---|---|---|---|---|
| 2,971,637 A * | 2/1961 | Simons | ........................ | 206/369 |
| 4,085,845 A * | 4/1978 | Perfect | ........................ | 206/564 |
| 4,256,457 A * | 3/1981 | Behring | ........................ | 433/77 |
| 4,306,862 A * | 12/1981 | Knox | ........................ | 433/77 |
| 4,353,694 A * | 10/1982 | Pelerin | ........................ | 433/77 |
| 5,172,810 A * | 12/1992 | Brewer | ........................ | 206/369 |
| 5,368,161 A * | 11/1994 | Plais | ........................ | 206/369 |
| 5,441,152 A * | 8/1995 | Estes | ........................ | 206/570 |
| 5,525,314 A * | 6/1996 | Hurson | ........................ | 422/300 |
| 5,626,227 A * | 5/1997 | Wagner et al. | ........................ | 206/369 |
| 5,692,609 A * | 12/1997 | Lin | ........................ | 206/368 |
| 5,829,590 A * | 11/1998 | Klein | ........................ | 206/369 |
| 5,913,422 A * | 6/1999 | Cote et al. | ........................ | 206/370 |
| 5,961,330 A * | 10/1999 | Hanson | ........................ | 433/173 |
| 6,036,490 A * | 3/2000 | Johnsen et al. | ........................ | 433/102 |
| 6,076,660 A * | 6/2000 | Day | ........................ | 206/63.5 |
| 6,328,565 B1 * | 12/2001 | Rose | ........................ | 433/77 |
| 6,612,435 B1 * | 9/2003 | Chang | ........................ | 206/373 |
| D526,064 S * | 8/2006 | Wood | ........................ | D24/229 |
| 7,328,796 B2 * | 2/2008 | Brunson et al. | ........................ | 206/373 |
| 7,451,870 B2 * | 11/2008 | Donahoe et al. | ........................ | 206/63.5 |
| 2002/0068255 A1 * | 6/2002 | Capt | ........................ | 433/77 |
| 2003/0073053 A1 * | 4/2003 | Brockway et al. | ........................ | 433/77 |
| 2005/0189250 A1 * | 9/2005 | Hsu | ........................ | 206/373 |
| 2006/0166165 A1 * | 7/2006 | Lehmann et al. | ........................ | 433/77 |
| 2006/0264822 A1 * | 11/2006 | Nagamatsu | ........................ | 604/97.02 |
| 2008/0166682 A1 * | 7/2008 | Bjorn et al. | ........................ | 433/77 |

* cited by examiner

*Primary Examiner* — Cris L Rodriguez
*Assistant Examiner* — Matthew Saunders
(74) *Attorney, Agent, or Firm* — Schwegman, Lundberg & Woessner, P.A.

(57) ABSTRACT

A storage device is provided for holding bone implant surgery articles. The storage device includes a body defining a plurality of openings capable of holding at least one rotatable drill bit that may be mounted on a drill and used to form a bore in bone and at least one implant container that holds an implant capable of being placed in the bore.

15 Claims, 4 Drawing Sheets

PROCEDURE SPECIFIC STORAGE BLOCK FOR HOLDING IMPLANT CONTAINERS AND SURGICAL TOOLS

FIELD OF THE INVENTION

The present invention relates to storage blocks that hold surgical instruments and, more particularly, to a dental storage block for holding various surgical instruments and implant containers used for a particular dental implant procedure.

BACKGROUND OF THE INVENTION

A dental implant or fixture is surgically implanted into the patient's upper or lower jaw bone to directly or indirectly anchor and support prosthetic devices, such as an artificial tooth. In order to install the implant, an implant site is prepared using conventional surgical procedures. Typically, an incision is made along the gingival tissue at the implant site and a bore is drilled into the patient's mandible or maxilla at the site using a drill and drill bits mounted on the drill called dental burs. Oftentimes, multiple dental burs of different shapes and sizes must be used to create a single properly sized and shaped bore.

To maintain sterilization, the implant is contained in a sterilized package or container often in the form of a vial with a flip open lid. The container may be held by a user with one hand while the user holds a driving tool in the other hand in order to engage and lift the implant out of the vial. Requiring two hands, however, can result in an awkward and inconvenient process during surgery. Once lifted, the implant is either threaded or press fit into the bore in the patient's jaw by using an implant driver to exert an apical force upon the end of the implant.

To store surgical tools, some known storage devices have a block with holes on the top of the block to receive and store only dental burs. The block and burs can be sterilized together through an autoclaving process. Some dental bur blocks contain a complex system with a reservoir compartment on the block which holds a volume of disinfectant fluid for sterilization of the burs.

Dental practitioners also need to verify the correct length of dental burs and/or implants being used for the surgical procedure. Often, the practitioner will use a drill to ensure implant length by comparing the known size of the drill with the size of the implant. A practitioner also may choose to measure the implant or dental bur using a separate periodontal probe or other instrument to verify the implant or bur length.

Thus, it can be understood that dental implant surgery, as well as any implant surgery, may require many separate surgical items in addition to dental burs, such as drills, implant containers, implant drives, bone taps, and measurement devices. Since the various surgical items mentioned above are separate components, the various items may be misplaced or difficult to maintain together at a close proximity to a patient readily available during a surgical procedure and in an order convenient to the surgeon. Therefore, it is desirable to have a storage device for implant surgery that solves the problems mentioned above.

DETAILED DESCRIPTION

Figure 1:
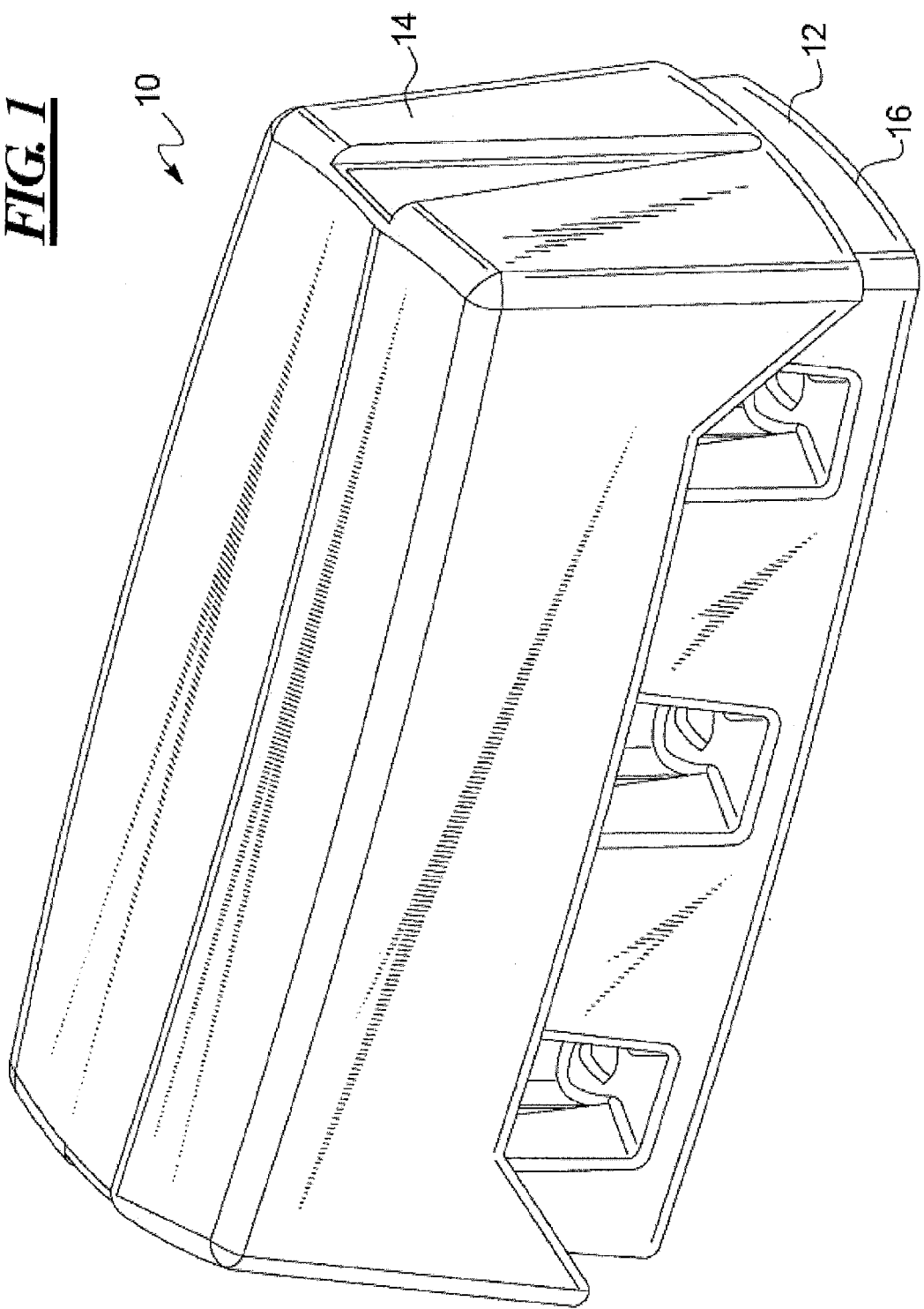
FIG. 1 is a front perspective view of the storage device embodying features of the present invention.
Figure 2:
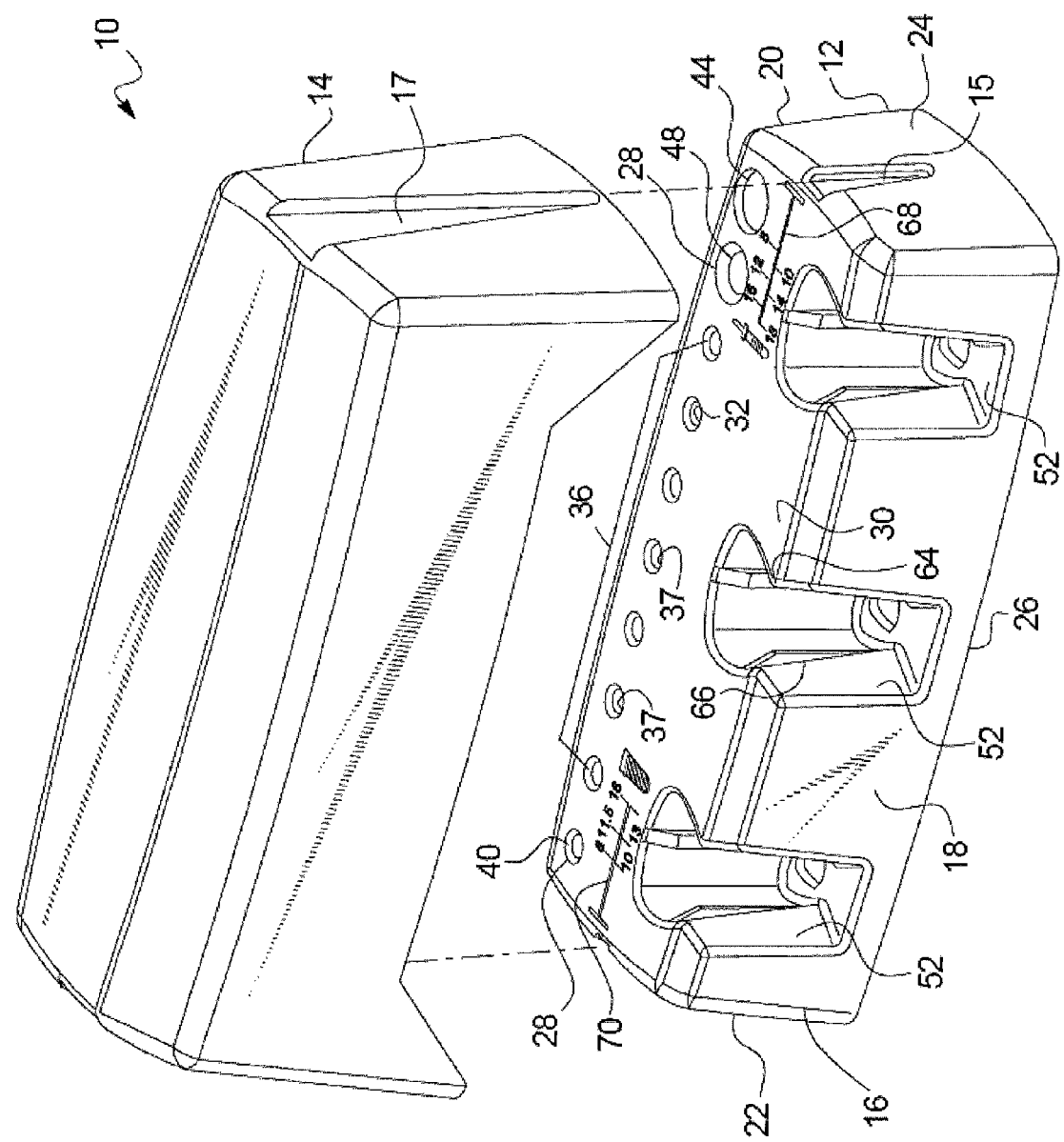
FIG. 2 is an exploded view of the storage device showing a storage block and lid embodying features of the present invention.
Figure 3:
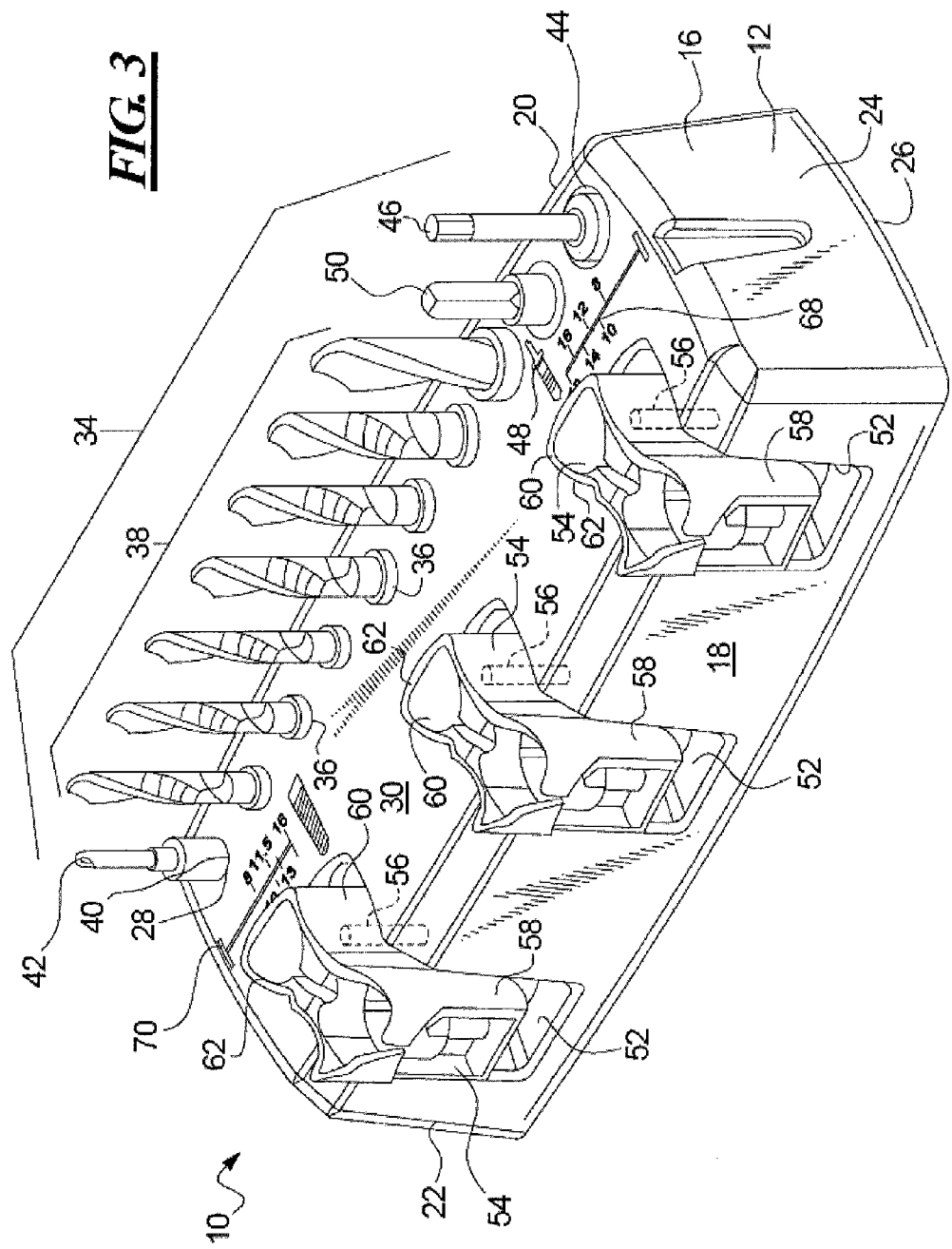
FIG. 3 is a front perspective view of the storage block holding surgical items and embodying features of the present invention.

Referring to FIGS. 1-4, there is illustrated a storage device 10 that holds and stores various dental instruments, tools, and accessories (herein referred to generally as "articles") needed for a surgical dental implant procedure. The storage device 10 provides a dental practitioner the ease and flexibility to have the necessary articles the practitioner needs to perform a surgical procedure readily available and in a close proximity to the patient. Moreover, the storage device 10 permits the practitioner to customize which articles are located on the storage device so that only those tools and accessories used for a particular surgery (such as a "patient-specific" surgery that requires tools of selected sizes) are located in the storage device. Also, the articles may be arranged within various openings in the storage device 10 in different orders convenient to the practitioner (such as burs being placed in order from left to right as the burs will be used during the surgery). The dental storage device 10 provides for efficient sterilization by allowing the entire storage device 10 and all its articles to be sterilized together at the same time thus eliminating the need to sterilize each piece individually, and efficiently only sterilizing articles needed for the procedure.

In more detail, the dental storage device 10 includes a storage block 12 and a lid 14. The storage block 12 has a body or base 16 made from opaque material such as injection molded RADEL® R polyphenylsulfone, generally available from Solvay Advanced Polymers of Alpharetta, Ga., as one example, and configured to hold and store the articles of many varieties. The body 16 has front, back, left, and right side walls 18, 20, 22, and 24. The lid 14 may have a translucent polymer material and can secure to the storage block 12 to provide cover for the articles held by the storage block 12. In one form, the lid 14 has an inwardly extending indent 17 received in a tight fit within an exteriorly facing groove 15 on the left and right side walls 22 and 24 of the body 16 to maintain the lid 14 in alignment with the block 12 as the lid is placed on, or removed, from the base. During a surgical procedure, the lid 14 can easily be removed from the storage block 12 to provide the practitioner access to the articles needed for the procedure.

The body 16 can be a single block of material with a flat bottom wall 26. It will be understood, however, that body 16 may alternatively be formed of a thin wall of material and is otherwise hollow such that it stands on bottom edges of the sidewalls 18, 20, 22, and 24.

The body 16 also includes multiple openings 28 located on an upper surface 30 of the storage block 12. The multiple openings 28 provide access to bores 32 and may be used to hold and store articles 34 that will be used during the surgical procedure. For example, at least one opening 36 can hold and store dental burs or drill bits 38 of different shapes and sizes that are necessary for drilling a bore in bone in a single specific surgical procedure. In one form, the openings 36 provide access to cylindrical bores 37 thereunder for holding the drill bits 38. When the drill bits or burs 38 come from the same set or are configured to attach to the same drill, the base or drill connection portion 35 (FIG. 4) of the burs 38 that is placed in bores 37 may all be the same size. In this case, the bores 37 all may have the same size to hold the burs 38. Likewise, the openings 36 and bores 37 may all have the same diameter and depth so that the largest drill bit 38 in a set of bits or burs 38 that have drill connection portions with varying dimensions may be maintained in an upright position with a portion of the drill bit 38 extending out of opening 36 and above body 16 where it is accessible to be grasped by a practitioner. So configured, any size drill bit in such a set of drill bits will still fit in any of the openings 36.

Of course, when the cylindrical bores 37 are sufficiently large, this also permits burs of different sets, makers, or brands to be placed in the bores rather than being limited to different sizes of burs from the same set. Alternatively, the bores 37 could have a certain shape with a predetermined changing inner diameter along the axial length of the bore 37 or other non-regular shape, for example, so that only burs or dill bits of a certain type or set will fit in a particular opening 36.

This structure provides the practitioner with the flexibility to customize and arrange the various burs 38 in any order the practitioner chooses. In one example, the openings 36 are arranged in a line generally near the back side wall 20. In this case the burs 38 may be placed from left to right in the order the burs 38 will be used during the surgical procedure. Of course, many other orders are contemplated such as by size, type of tip shape, and so forth as selected by the practitioner. Also, all of the openings 28 may be arranged on upper surface 30 in any configuration other than a straight line that is practical or convenient to the practitioner.

Whether or not the openings 36 are configured to receive a particular drill bit 38, the upper surface 30 of the body 36 may have indicia near each opening 36 to identify the intended drill bit 38 for each opening 36.

In a similar manner to the openings 36, at least one opening 40, and in turn the bore it opens to, is provided to receive a drill 42 that the drill bits 38 are mounted upon. At least one opening 44 may be used to hold an implant driver 46. The implant driver 46 is used to drive the implant into the bore of the implant site. Openings for different sized implant drivers 46 may also be provided on storage block 12 when multiple drivers are used with a surgical procedure for inserting multiple implants of different sizes and shapes, for example. At least one opening 48 receives a bone tap 50. The bone tap 50 is used to pre-thread the bone within a drilled bore to receive an implant. A variety of different bone taps may be used in a single surgical procedure and spaces on storage block 12 for such multiple bone taps may also be provided. The openings 40, 44, and 48 may all be sized or shaped as similarly mentioned above for the drill bit openings 36 so that multiple articles used for the particular procedure are placed on storage device 10 in an order convenient for the practitioner.

It also will be understood that openings 36, 40, 44, and 48 can be configured and sized to hold and store any other dental surgical instrument that is needed to complete a dental surgical procedure such as scalpels or measurement devices, for example.

Openings 28 also include recesses 52 extending inwardly from the front side wall 18 and upper surface 30 on the storage block 12. The recesses 52 hold implant containers or vials 54. The vials 54 can provide a sterilized atmosphere to store implants 56 (shown in dashed line) during a surgical procedure until they are needed. The storage block 12 can hold the vial 54 in a position sufficient to permit access to the implant 56 by a tool, such as driver 46, for sanitary removal of the implant 56. Specifically, in one form, the vial 54 has a flip open top with a hinged cap 58 mounted on a main body 60 of the vial. In the open position with the cap 58 off of the main body 60, an opening 62 in the upper end of the main body 60 exposes the implant 56 for engagement and removal by a driver 46 or other tool. In some implant container designs, the cap 58 holds a retaining screw for securing a prosthetic device such as an abutment to the implant. In this case, the flipped open position also exposes the retaining screw in the cap for removal by a tool.

The vial 54 is positioned snugly within the recess 52 to permit the insertion of the implant driver 46 to engage and remove the implant 56 from the vial 54 while the vial 54 remains steady and secured within the recess 52. The vial 54 is secured within the recess by a tight or friction fit or by a groove and pin/indent-type connection between the body 16 and vial 54. The recess 52 has opposite and inwardly protruding side walls 64 and 66 that form a width 'w' therebetween that is less than the maximum width 'W' of the vial 54 as shown on FIG. 4. This structure retains the vial 54 in the recess 52 in the forward direction (i.e., from moving toward and out of front well 18). For some vial configurations, when the vial 54 is in a fully open position, the cap 58 can lock onto a side wall of main body 60 typically by a slot/pin type connection between the cap 58 and main body 60. In this case, the protruding side walls 64 and 66 are secured horizontally between the main body 60 and cap 58 of the vial 54 to further secure the vial 54 to the storage block 12.

The entire storage block 12 can be sterilized with the articles 34 it holds, making it unnecessary to sterilize an entire surgical kit. Typically, the storage block 12 is sterilized by undergoing high temperature autoclaving. When the storage block 12 only holds articles 34 to be used in the surgical procedure, energy is not wasted sterilizing tools that will not be used, and the unused instruments in this surgical kit are not exposed to unnecessary autoclaving preserving their useful life.

Figure 4:
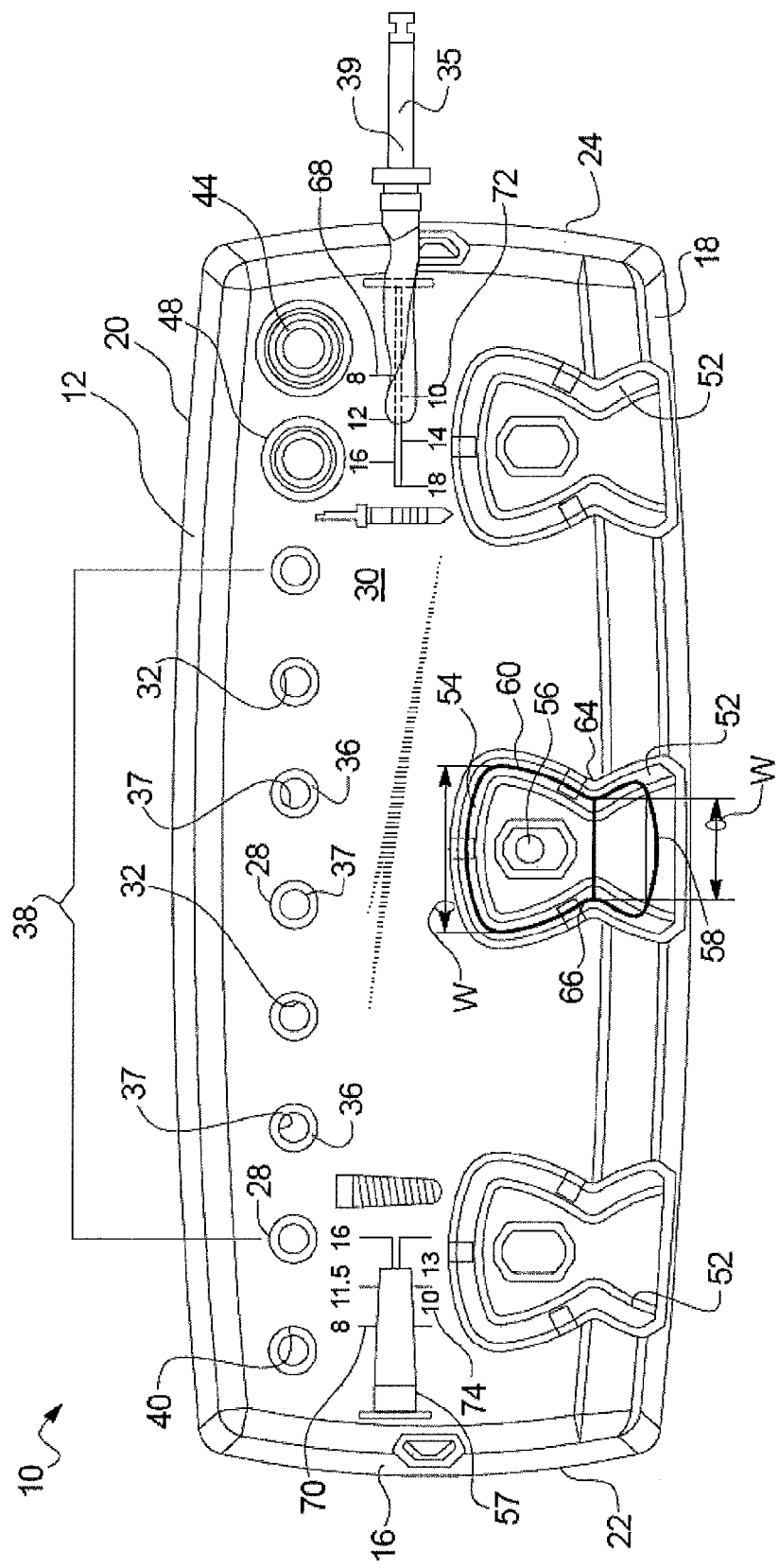
FIG. 4 is a top plan view of the storage block shown with an implant and bur over the storage block and embodying features of the present invention.

Referring to FIG. 4, storage block 12 also is provided with measurement scales 68 and 70 on the upper surface 30 that can be used to measure dental burs or implants. This proximity of the measurement scales 68 and 70 permits the practitioner to readily measure and verify the drill depths of the dental bur implant length without the need for separate tools to do so. To measure the bur 39 or implant 57, the practitioner will position the dental bur 39 or implant 57 respectively over the measurement scales 68 or 70. Measurement scales 68 and 70 can be engraved, inscribed, or otherwise marked onto the upper surface 30 or any of the other side walls of the body 60 if convenient. The scales 68 and 70 have numerical markings 72 or 74 incremented in various intervals so that the precise length of the dental bur 39 or implant 57 can be determined.

In operation, the storage block 12 is loaded with articles 34 for a patient-specific surgical implant procedure and in an order (such as from left to right) convenient for the practitioner. The storage block 12 with the articles 34 may then be sterilized, and implant containers 54 are then mounted on storage block 12. During the procedure, the practitioner conveniently removes the tools, whether a drill, drill bit, driver, bone tap, or other tool, as well as implants mounted in the storage block 12 as needed. After or during the surgery, the dirty articles can be placed back in the storage block 12, which can then all be cleaned and returned to the surgical kit or storage block for sterilization together.

It will be understood that while the storage device 10 is mainly described herein for use with a dental surgical procedure, it will be understood that the storage device may be used with other bone implant surgeries used on other areas of a human body or an animal.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept. Further, this application is intended to cover such departures from the present disclosure as come within known or customary practice in the art to which this invention pertains and which fall within the limits of the appended claims.

What is claimed is:

1. A storage device for holding bone implant surgery articles, comprising:
    a body having a front wall, an upper surface, a lower surface, and defining a plurality of openings, including:
        at least one drill bit opening formed in the upper surface and extending towards the lower surface in a direction generally perpendicular to the upper and lower surfaces, the at least one drill bit opening configured to hold in an upright position at least one rotatable drill bit being mountable on a drill for forming a bore in bone; and
        at least one container opening formed in the upper surface and extending towards the lower surface in a direction generally perpendicular to the upper and lower surfaces, the at least one container opening configured to hold in an upright position at least one implant container for holding an implant to be placed in the bore; and
        at least one front wall opening in communication with the at least one container opening, wherein the at least one front wall opening comprises a recess having opposite side walls that are inwardly protruding towards one another to form a width less than a maximum width of an implant container.

2. The storage device of claim 1 wherein the body has an exterior surface with measurement scales for measuring an implant or drill bit.

3. The storage device of claim 1 wherein the at least one front wall opening is shaped to secure the implant container in an open state sufficient for providing access to the implant with a tool for engaging and lifting the implant.

4. The storage device of claim 1 wherein the plurality of openings further include at least one opening configured to receive at least one drill.

5. The storage device of claim 1 wherein the plurality of openings are configured to receive at least one implant driver configured for engaging the implant.

6. The storage device of claim 1 wherein the plurality of openings further include at least one opening configured to receive at least one bone tap.

7. The storage device of claim 1 wherein the body is made of a sterilizable material.

8. The storage device of claim 1 wherein all of the articles configured to be stored on the body are selected for a particular, patient-specific implant surgery.

9. The storage device of claim 1 wherein the at least one drill bit comprises a plurality of drill bits selected from a set of drill bits.

10. The storage device of claim 1 wherein the bone implant surgery articles comprise dental implants configured to be implanted in a jaw bone.

11. A storage device for holding dental implant surgery articles, comprising:
    a storage block having a front wall, a back wall, side walls and an upper surface,
    the storage block defining openings in the upper surface specifically shaped for holding in an upright position:
        at least one drill for forming a bore in bone;
        a plurality of drill bits mountable on the drill;
        at least one implant container holding an implant; and
        at least one driver for driving the implant into the bore; and
    at least one measurement scale disposed on the storage block for measuring the size of the implant or the drill bit;
    wherein an opening for the at least one implant container communicates with an opening extending inwardly from the front wall,
    wherein the at least one drill, the plurality of drill bits, the at least one implant container, and the at least one driver are specifically selected and arranged on the storage block for a particular patient-specific implant surgery, and
    wherein the opening extending inwardly from the front wall comprises a recess having opposite side walls that are inwardly protruding towards one another to form a width less than a maximum width of an implant container.

12. The storage device of claim 11 wherein the openings further comprise at least one opening specifically sized to receive at least one bone tap.

13. The storage device of claim 11 wherein the storage block is made of a sterilizable material.

14. The storage device of claim 11 wherein the at least one implant container is positioned within the recess and engaged therein by one of a friction fit and a groove and pin connection.

15. The storage device of claim 11 wherein the at least one implant container has a flip open top with a hinged cap.

* * * * *